(12) United States Patent
Göbel

(10) Patent No.: US 7,691,079 B2
(45) Date of Patent: Apr. 6, 2010

(54) DEVICE FOR TAMPONADE OF BODY CAVITIES AND MECHANICAL ANCHORING OF A CATHETER

(75) Inventor: Lothar Göbel, Würzburg (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 523 days.

(21) Appl. No.: 10/545,191

(22) PCT Filed: Feb. 7, 2004

(86) PCT No.: PCT/EP2004/001139

§ 371 (c)(1),
(2), (4) Date: Aug. 10, 2005

(87) PCT Pub. No.: WO2004/069057

PCT Pub. Date: Aug. 19, 2004

(65) Prior Publication Data

US 2006/0184109 A1    Aug. 17, 2006

(30) Foreign Application Priority Data

Feb. 10, 2003  (DE) ............................. 103 05 553

(51) Int. Cl.
*A61M 29/00* (2006.01)
(52) U.S. Cl. ................. 604/96.01; 604/103.11
(58) Field of Classification Search ........... 604/96.01, 604/103, 103.05, 103.06, 104, 910, 912, 604/918, 103.02, 103.07, 103.1, 103.11, 604/174

See application file for complete search history.

(56) References Cited

U.S. PATENT DOCUMENTS

| 2,324,520 | A |   | 7/1943  | Lamson |
|-----------|---|---|---------|--------|
| 3,802,418 | A |   | 4/1974  | Clayton |
| 4,850,953 | A | * | 7/1989  | Haber et al. ............... 600/32 |
| 5,409,006 | A | * | 4/1995  | Buchholtz et al. ......... 600/439 |
| 5,545,179 | A | * | 8/1996  | Williamson, IV .......... 606/213 |
| 5,643,178 | A |   | 7/1997  | Moll et al. |
| 5,667,479 | A |   | 9/1997  | Kieturakis |
| 5,935,107 | A | * | 8/1999  | Taylor et al. ............ 604/164.04 |
| 2002/0165553 | A1 | * | 11/2002 | Elbert et al. ............ 606/108 |

FOREIGN PATENT DOCUMENTS

| DE | 195 08 129 | 9/1996 |
| EP | 0 624 349 | 11/1994 |
| EP | 1 097 675 | 5/2001 |

* cited by examiner

*Primary Examiner*—Nicholas D Lucchesi
*Assistant Examiner*—Theodore J Stigell
(74) *Attorney, Agent, or Firm*—Dority & Manning, P.A.

(57) ABSTRACT

A device for tamponade of body cavities and for mechanical anchoring of a catheter, the device including a flexible tube segment (2) having an inner wall (4) and an outer wall (6) that surround an interior space (8), wherein the tube segment (2) is inflatable, and is configured without through-passing support bodies so that a displacement of tube wall material between the inner wall (4) and the outer wall (6) of the tube segment (2) is possible by inflation of the tube segment, wherein the tube segment is provided with two ends (7,9), which are fastened to a same closing element (10), configured so that a torus geometry is striven for as the inflatable tube segment (2) is inflated and the closing element (10) is a pipe nipple and the two ends (7,9) of the tube segment (2) are joined together fluid-tightly.

27 Claims, 3 Drawing Sheets

DEVICE FOR TAMPONADE OF BODY CAVITIES AND MECHANICAL ANCHORING OF A CATHETER

CROSS-REFERENCE TO RELATED APPLICATIONS

This application claims priority to International Application Serial No. PCT/EP04/001139, field Feb. 7, 2004, which claims priority to German Patent Application No. 103 05 553.3, filed Feb. 10, 2003.

TECHNICAL FIELD

The invention is concerned with a device to be used in healing processes as set forth in the preamble to Claim 1.

Devices that serve to tamponade cavities are known in medical technology. The devices are composed of inflatable elastic hollow bodies. Various sizes of these hollow bodies are known, so that they can be used to seal ostia of different sizes. Also used are devices whose outer contour is shaped so that they are able to fill a cavity completely when inflated.

In tamponade, especially of spaces in biological tissue, the problem arises that the tamponade device may not be fully adapted to the shape of the cavity and may exert undesirable pressure on adjacent mucosa. This problem is exacerbated by the fact that the tamponade balloon is designed without a residual volume and high restoring forces are present with the wall material used. In tamponade of the nasal cavities, a further problem is that these cavities have a strictly centrally controlled, locally uninfluencable system of nasal conchae, which exhibits periodic circadian pressure fluctuations that add to the internal pressure of a tamponade balloon that has no residual volume, thereby increasing the risk that tamponade will curtail vascular perfusion of the adjacent tissue. In view of the widely varying size ratios of the paranasal sinuses and the breadth of interindividual variation in the spatial configuration and volume of anatomical spaces, a large number of anatomically preformed devices is needed. This is very cost-intensive.

In addition to the known devices for tamponading ostia and/or cavities, catheters composed of an elastic catheter shaft and a fillable balloon element mounted thereon are also used in medical technology. The catheter shaft comprises a filling channel that opens into the interior of the balloon through a port in the catheter wall. The balloon element itself serves primarily to anchor the catheter mechanically in a secure manner. It also often has a sealing function and prevents, for example, urine from leaking out of the bladder past the catheter through the urethra. The balloon fastened to the catheter strives to assume a spherical shape when filled with a fluid. The largest cross section of the balloon therefore exceeds the cross section of the ostium of the cavity and thus prevents retraction by conforming to the rim of the cavity opening. The spherical shape of the balloon is unsatisfactory for performing the holding and sealing function, since under tensile stress it has a tendency to assume a spindle shape and slip into the ostium, causing the securement of the device and the relatively small sealing contact area between the balloon wall and the rim of the cavity ostium to be lost. This is a particularly significant problem in connection with biological tissues, since the ostia of body cavities usually do not have a fixed width. For this reason, more or less broad-area retaining disks of rigid material have been mounted on the catheter shaft, but owing to their bulky construction they cannot be used with small ostia in the millimeter range. In addition, the spherical balloon requires the supporting body that passes through it, i.e., the catheter shaft, which can be very troublesome particularly in tight spaces.

PRIOR ART

EP 0 624 349 B1 discloses a device for tamponading and keeping open body cavities and passages delimited by bone after surgical manipulation, in which the outer shape of the balloon, in the fluid-filled state, is adapted to the inner shape of the body cavity. In this device, the balloon is implemented as a catheter shaped in anatomically idealized fashion and is adapted, in a wedge shape, to the human frontal sinus or ethmoid sinus. The chief disadvantage of this device is the large number of sizes needed due to the broad variation in shape of these spaces.

DESCRIPTION OF THE INVENTION

The object of the invention is to create a device to be used in healing processes that avoids the disadvantages recited above and can be used in a versatile manner. The device schall be usable, insofar as possible, both for tamponading and for catheter insertion. Finally, it is intended to be as inexpensive as possible to make and to be usable for both applications with respect to the naturally occurring sizes of the cavities.

The set object is achieved according to the invention by means of the features of Claim 1. Dependent Claims 2 to 27 reflect advantageous improvements of the idea of the invention set forth in Claim 1.

The fashioning of the device as a flexible, double-walled, inflatable tube segment affords the possibility of a broad field of application. The device is, in addition, very easy to make.

In the simplest embodiment, the tube segment is formed by an inner wall and an outer wall that surround a hollow space, at least the outer wall being thin-walled and elastically expandable. When a fluid, i.e. a liquid or a gas, is introduced into the tube segment, the outer wall of the tube segment unfolds and thereby lies against the walls of the ostium or the walls of a cavity that is to be filled. The unfolding and elastic expandability of the outer wall serve to adapt the outer wall fully to the spatial conditions.

It is advantageous if the tube segment is made of a transparent material. Particularly suitable materials that may be contemplated for this purpose are polyurethane, or a polyurethane/polyvinyl fluoride-containing mixture or a comparable polyurethane-based material or a polymer having comparable expansion and processing characteristics. The tube segment can be made especially thin-walled with these materials. The desirable wall thickness is in the micron range, specifically preferably 5 to 15 µm. In addition, a probe can be inserted into the tube segment from the outside and the cavity observed from the inside. Such a tube segment can be used both for tamponade of cavities or ostia and for the reversible, sealing securement of catheters, by being disposed at the end of a catheter.

By virtue of its characteristics, the device is particularly well suited for tamponade of natural or artificially created ostia. Catheters can also be well secured in hollow organs such as the urinary bladder, stomach or intestine. The novel securement also results in better sealing with respect to the opening of the cavity than would be possible with a spherical balloon, since sealing contact is made, not with a relatively small area of the cavity wall immediately adjacent the ostium of the cavity, but rather with a much larger contact area constituted by the proximal toroidal bulge provided by the tube segment. When the inflatable tube segment is filled with the fluid, a longitudinally extending torus is formed that has especially favorable sealing properties.

The production of the tube segment takes place in a particularly favorable manner by the invagination of a single-walled tube section. A tube section of a set length, for example 10 cm, is tucked into itself so that the two ends of the tube section roughly coincide. The ends can then be fastened to a terminating device in the form of a pipe nipple, or alternatively to a suitable location on a catheter. A channel for delivering and/or discharging fluid is inserted into the interior space produced by the walls of the tube segment formed in this way. If a fluid is introduced into the interior space of the tube segment, then the outer wall of the tube segment unfolds and expands and can be used, as appropriate, for tamponade or for securing a catheter.

In order to achieve the particularly good mode of action of the subject matter of the invention, the tube segment is preformed as a single-walled tube before being shaped by invagination. This preforming is preferably executed in such a way that the portion of the tube forming the outer wall of the tube segment after invagination forms a torus swollen in the plane of rotation of the tube segment when inflated. The extent of the preforming can vary, that is, after preforming and invagination, the outer wall of the tube segment lies more or less folded against the inner wall thereof. It is also possible for at least the end wall that adjoins the outer end of the tube segment and is present after inflation to be fashioned as thicker in the preforming operation, in order to achieve an improved sealing action for special cases.

Quite generally, the preforming of the single-walled tube is executed in such a way that the portion of the tube that forms the inner wall of the tube segment after invagination has a smaller cross section and a greater wall thickness than the tube portion that forms the outer wall after invagination.

Quite generally, it is also provided that the device is shaped so as to have a residual volume relative to the volume of a body cavity that it is to be tamponaded by it, i.e., the tube segment in the freely unfolded state has a greater volume than the body cavity to be tamponaded.

The wall thickness, at least of the outer wall of the tube segment, is in the range of a few microns to enable the outer wall to unfold satisfactorily. The folds formed by excess wall material when the device is unfolded in a cavity to be tamponaded by it are capillary-sized. Fluids are thus retained therein by virtue of adhesion forces.

The channel opening into the interior of the tube segment is connected via a flexible connecting tube to a valve disposed outside the tube segment. The valve can be fashioned as a lip valve. It is also possible, however, to provide the channel with a circular cuff made of flexible material, which keeps the fluid from flowing backward out of the interior space of the tube segment.

It can be advantageous in some applications if the outer wall of the tube segment is formed of a polar, slightly water-permeable material. This material can be a semipermeable membrane, for example.

Fashioning the device as a tube segment also makes it possible to place a pressure sensor in the interior space of the tube segment to measure transmural pressure during inflation. Excessive pressures during the inflation of the device can be detected and avoided in this way.

So that the fluid does not inadvertently escape from the interior space of the tube segment, a valve is disposed at a suitable location in the channel. Various types of construction are possible here, in terms of both the design of the valve and its placement location in the channel.

According to a variant, a clamping closure that has a longitudinally displaceable sleeve for partially or completely occluding the channel can be slid onto the tube segment. This sleeve can, by being displaced, simultaneously define the size of the tube segment itself.

Finally, a collar-shaped abutment can be disposed on the pipe nipple or the catheter shaft for clamping and securing a cavity wall on the tube segment.

The tube segment satisfies securing and sealing requirements by means of the ideal torus geometry that it strives to assume during inflation. When deflated, the tube segment can be stretched out longitudinally in folds in a manner that enables it to be inserted through very narrow openings. The tube segment can, if necessary, be equipped with a guide rod or a guide tube as a positioning aid. However, when deflated, the stretched-out double tube body does have a certain rigidity, due to the close mutual contact of four wall layers, that alone makes it possible to position it for most applications. This self-supporting effect can be enhanced by fashioning the invaginated portion of the tube wall as thicker-walled than the rest of the tube segment.

When the proximally or distally united ends of the tube are inflated along the stretched-out tube segment, a relative movement of the ends of the tube walls and the tube body occurs. As inflation proceeds, the material of the tube walls is displaced between the portions of the tube close to and those remote from the axis of rotation, which displacement begins at that moment when the two parts of the tube facing the axis of rotation come into contact, and is maintained until the united ends of the tube walls have come as close as they can to the center of rotation of the unfolded torus and the most energetically favorable geometry for the inflated tube segment has therefore been assumed.

If the two united ends of the tube are then secured outside the wall of the cavity, the tube segment with its annular bulge conforms to the wall of the cavity and presses the wall against the collar-shaped abutment. The tube segment is held in position for as long as the internal pressure is maintained.

If the tube segment is stretched out proximally in the deflated state, then inflation results in a distal movement of the tube segment that is suitable for unfolding the tube segment into a cavity. The tube segment is also suitable for expelling substances from a cavity in this way.

Because of its thin-walled and residual-volume design that spares a through-passing support body, the tube segment is suitable in particular for tamponading structurally complex spaces or spaces containing a pressure-sensitive mucosa, such as, for example, the nasal cavity and the paranasal sinuses. It therefore lends itself to general applications in which the internal pressure must be transmitted directly to the wall of the body cavity, without the addition of any retraction force of the wall material of the tube segment, so that in this way the pressure exerted directly on the surrounding tissue can be measured by means of a manometer connected externally to the channel to make certain that the vascular perfusion pressure of the adjacent tissue is not exceeded by the tamponade. The toroidal shape of the tube segment further makes it possible to place a pressure sensor in the interior space between the tube portions of the double-tube body that are near the axis of rotation without thereby exerting a disruptive effect on the interface with the surrounding tissue. Given the residual volume of the tube segment, the pressure measured at that location corresponds to the pressure transmitted to the surrounding tissue via the tube portions remote from the axis.

If the tube segment is equipped with a thin wall of polyurethane through which water "leaks" in small quantities, the tube segment can also be used to drain cavities or alternatively for the prolonged delivery of polar drug active ingredients, such as for example $N_2O$, through the wall from inside to outside. It is, of course, equally feasible to utilize such effects in the opposite direction.

The inventive combination of residual dimensioning of the balloon, microthin-walled construction for the balloon envelope, and the shaftless and catheterless tamponade tube makes the device according to the invention also suitable for the introduction of radiating media in a manner that is tolerated by the blood circulation and does not inhibit perfusion, for example to obliterate proliferating tissue in chronic inflammatory processes or for preoperative tumor reduction. The tamponade body enables even complexly shaped, bony cavities, such as for example the paranasal sinuses, to be completely filled with a radiating medium in a manner that is tolerated by the tissues, and in which the transmural force exerted on all surfaces of the cavity is nearly homogeneous and causes no significant impairment of tissue perfusion and the medium can subsequently be removed conveniently and completely from the cavity. Whereas heretofore such media were introduced freely into the body cavity and usually could not be retrieved completely after treatment, the present tube tamponade device thus enables the radioactive substance to be removed completely by evacuating the tamponade device and then simply withdrawing the entire body thereof. Its use in nuclear medicine can additionally be contemplated, in the long-term, perfusion-compatible irradiation of tumor tissue in the brain, breast, intestine, intraabdominal and intrathoracic organs, and, of course, surgically opened or created body spaces. To avoid inadvertent exposure of tissue outside the area to be treated, the tamponade device can be protected by suitable partial sheathing and/or by shielding with a material that is opaque to the radiation. The material can be a metal and can be implemented as a separate layer or as a direct component of the tube segment, for example in the form of a metallic layer vapor-deposited thereon.

In addition to the ability of the tube tamponade device to be used in radiation therapy and nuclear medicine, radiodiagnostic use thereof can also be contemplated. Instead of a radioactive substance, radiopaque contrast media can be introduced into the tamponade body in order to visualize body cavities or organs in toto and to avoid exposing the tissue directly to the substance and preclude systemic uptake of the substance by the organism.

If it is equipped with an internal valve mechanism, the tube segment can be detached from the fluid feed after inflation. This makes it possible to disconnect the tube segment from bothersome delivery lines when it is in the inflated state, e.g. when the tamponade device is inserted in the nasal cavity, and to secure the proximal end of the closure externally, on the surface of the body. This can be done by means of the clamping closure with its two longitudinal slits, the closure being wholly or partially retracted and spread over the terminating device during this retraction, if the clamping closure is designed so that it is not split over its entire length, but distally comprises a closed tube portion that surrounds the still folded together material of the tube wall, and if proximally its displaceability relative to the tube portion that is disposed beneath it and is not unfolded can be set in any desired position by means of a sleeve.

For the special case of nasal tamponade after a nasal septum operation, the tube segment can be used by equipping it in its central lumen with a brace that gathers the unfolded, cylindrical, double-tube body together at one end and thus permits a planar bearing surface in the nature of a splint for the nasal septum, the splinting being maintained by tamponading the remaining space of the nasal cavity with the now cushion-like opposite portion of the tube segment. The leg of the U-shaped splint that is in contact with the nasal septum can additionally serve as a carrier for therapeutic agents and be secured to the terminating device to maintain the gathering of the tube wall material.

The inventive relative movement between the inflated tamponade tube and the pipe nipple for securing the tube makes it possible to use the present tube tamponade in a particular manner to seal the anus in patients with rectal incontinence syndrome. The annular bulge that forms when the tamponade body is filled conforms to the rectal sphincter from the inside and seats on it like a sealing cap. If the nipple securing the ends of the tube is placed outside the body and there connected to an abutment that holds the securing nipple in the anal fold and keeps the nipple from slipping into the rectum or anus, the contrary movements of the unfolded tamponade tube and of the extracorporeal securing element result in compressive sealing of the balloon body on the floor of the rectum and thereby counteracts incontinence.

The abutment can be implemented in the form of an anchor-like tube element or rod element disposed substantially at right angles to the balloon body, or as an independent balloon that seats on the securing nipple and, as a possible variant embodiment, is supplied concomitantly via the filling lumen of the inner balloon. A draining or feeding catheter can in turn be inserted through the free, open lumen of the tucked-in tamponade balloon and a suitably shaped securing nipple.

The tube segment can also serve to bring substances or bodies affixed to its surface into direct contact with the body cavity in order to focus therapeutic effects on the site to be treated. It is, as shown schematically in FIGS. 1 and 2 for example, possible to attach outwardly conducted electrodes 25 via leads 26 to the surface of the tube segment in order to stimulate body tissue with an electrical voltage or pick up and measure voltages that are present there. The electrodes 25 are made of metal, per standard practice. They can be adhesive-bonded or vapor-deposited.

It is further possible for one or more bodies such as receptacles or carriers containing radioactive or chemotherapeutic agents to be fastened to the tube segment. Such receptacles or carriers can be pressed directly against the site to be treated, which facilitates targeted treatment and makes it easier to prevent inadvertent secondary injury to surrounding healthy tissue.

BRIEF DESCRIPTION OF THE DRAWING

The invention is described in further detail below with reference to several exemplary embodiments.

In the drawing.

EXECUTION OF THE INVENTION

Figure 1:
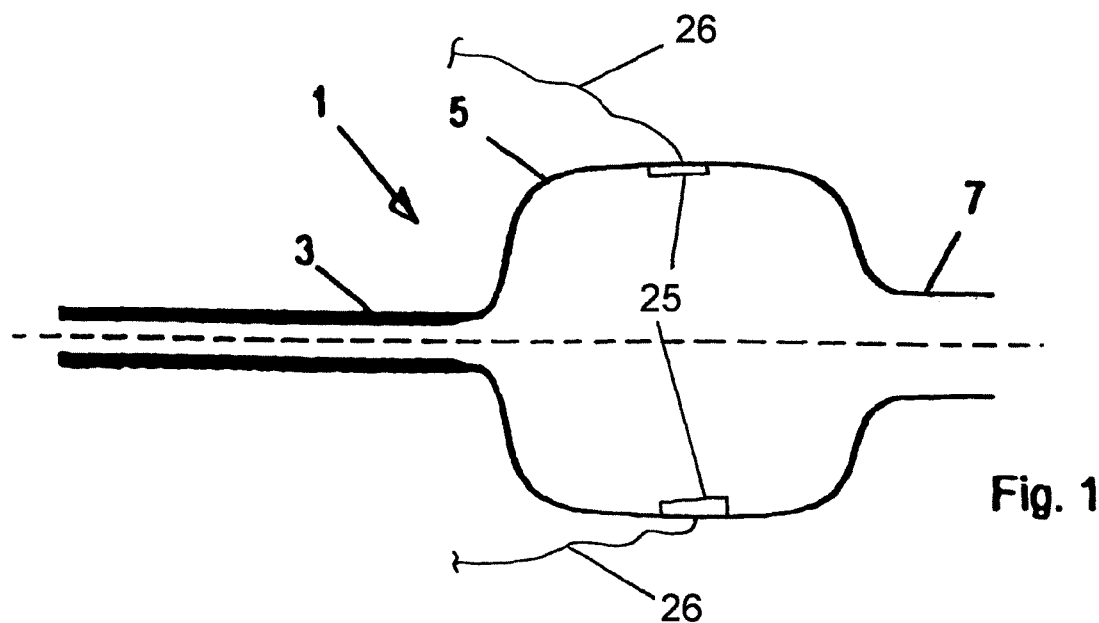
FIG. 1 is a schematic depiction of a preformed tube section.

Illustrated in FIG. 1 is a tube section 1 preformed for making a tube segment 2. Tube portion 3, which forms the subsequent inner wall 4 of tube segment 2, is unchanged as to wall thickness and inner and outer diameter. By contrast, tube portion 5, which forms the subsequent outer wall 6 of tube segment 2, is considerably widened, whereby the wall thickness has diminished greatly. Tube end 7 adjacent this tube portion 5 is also partially widened. This preforming is carried out in heatable forming installations. A transparent polyurethane is used as the material of tube section 1 and thus tube segment 2.

Figure 2:
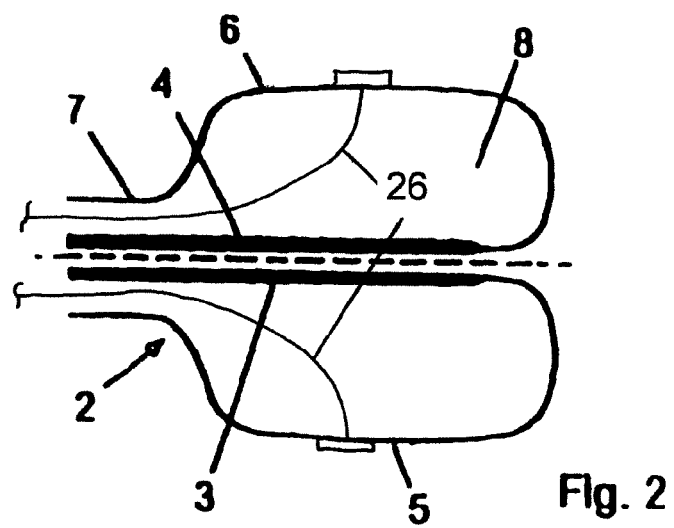
FIG. 2 shows the preformed tube section of FIG. 1, shaped into the tube segment by invagination.

To form tube segment 2, the relatively stable tube portion 3 is pressed into the interior space of tube portion 5 and tube end 7 is rolled over, thereby producing the shape illustrated in FIG. 2.

FIG. 2 illustrates the shape of a tube segment 2 when unfolded. For this purpose, a fluid is filled into the interior space 8 bounded by inner wall 4 and outer wall 6. When the interior space is emptied, outer wall 6 lies in the folded-up state against inner wall 4.

Figure 3:
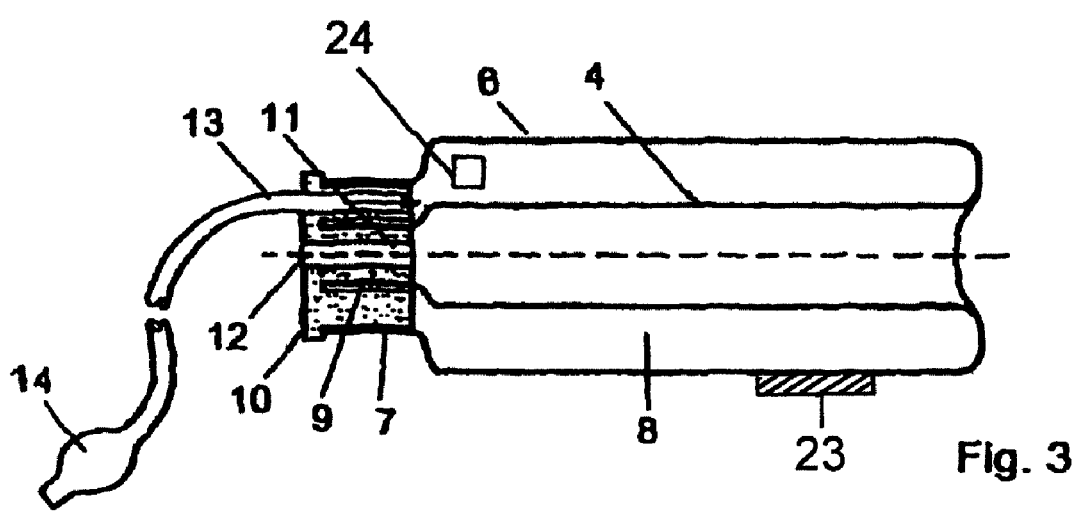
FIG. 3 is a longitudinal section of an inflated tube segment.

FIG. 3 shows a practical exemplary embodiment of tube segment 2 that can be used for tamponading. Both ends 7 and 9 of tube segment 2 are grasped fluid-tightly by terminating device 10. Terminating device 10 is fashioned in the form of a pipe nipple. Opening 11 in the center of pipe nipple 10 can be occluded with a stopper 12. It is also possible, however, to insert a catheter shaft into opening 11. Interior space 8 of tube segment 2 is connected to a channel 13 provided for the delivery and/or discharge of a fluid. Tube segment 2 is shown inflated and greatly enlarged. Installed in channel 13 is a valve 14 that prevents the inadvertent outflow of fluid from interior space 8. In the example, valve 14 is formed by a lip valve that is known per se, with valve lips that lie against each other elastically. As schematically shown in FIG. 3, a pressure sensor 24 can be placed in the interior space 8 between the tube portions of the double-tube body that are near the axis of rotation without thereby exerting a disruptive effect on the interface with the surrounding tissue.

Affixed locally to the surface of tube segment 2 is a body 23 containing a chemotherapeutic or radioactive substance. When the tube segment is in the inflated state, said body is pressed together with the body site to be treated, thus making it possible to develop an especially concentrated efficacy locally while avoiding injury to surrounding healthy tissue.

Figure 4:
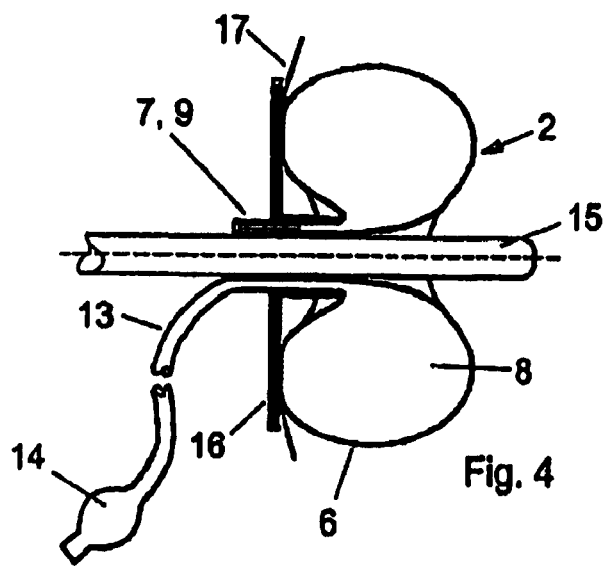
FIG. 4 is a schematic longitudinal section through another embodiment of a tube segment on a catheter.

FIG. 4 shows an exemplary embodiment in which tube segment 2 is placed on the end of a catheter 15. The ends 7, 9 of tube segment 2 are connected, one surrounding the other, to catheter tube 15. Channel 13 leads into interior space 8 of tube segment 2. The example shows the placement of tube segment 2 in a cavity that is not delineated in more detail. In this case, an annular abutment 16 can be placed like a collar on catheter shaft 15, so that, for example, the skin 17 at the opening to the cavity can be clamped sealingly between abutment 16 and outer wall 6 of tube segment 2. Such an implementation makes it possible, for example, to flush out a body cavity with a liquid in a controlled manner. Contamination of the environment is prevented by the annular abutment lying sealingly against the skin.

Figure 5:
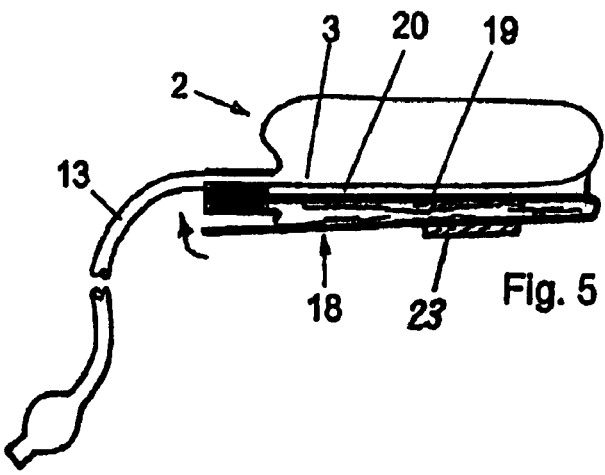
FIG. 5 is a longitudinal section of a tube segment with a brace inserted.

FIG. 5 shows the use of tube segment 2 with the simultaneous application of a brace 18. Brace 18 is made of rigid material and is pushed by its one leg 19 into the free space 20 of tube portion 3. By means of brace 18, tube segment 2 can be provided with a rigid portion on a desired side. It can also be used to carry substances or bodies 23 affixed to its surface and to place them in a body cavity in a targeted manner and use them for chemical or therapeutic treatment. In this context, the gentle pressing together with the body caused by the tube segment applied to the back and inflated during use is of crucial importance for the success of the treatment. Correct and precise positioning of the body in the cavity is particularly easy to achieve.

Figure 6:
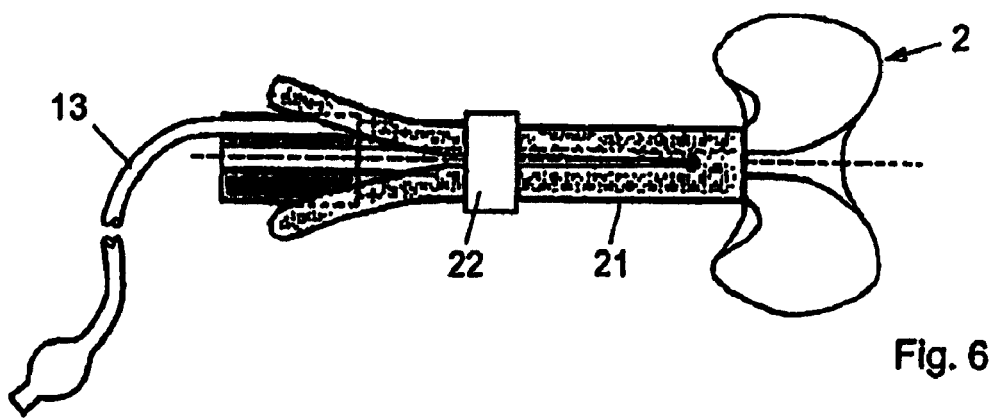
FIG. 6 illustrates a tube segment with a clamping closure slid thereonto.

FIG. 6 shows a form of use of tube segment 2 in which a clamping closure 21 is slid onto tube segment 2. The size of the inflated portion of tube segment 2 can be defined by displacing clamping closure 21 along tube segment 2. The farther clamping closure 21 is slid to the left as seen in the drawing, the larger the released portion of tube segment 2 becomes. Clamping closure 21 is intended to be secured by means of a sleeve 22 that can also be displaced longitudinally. Clamping closure 21 is split over almost its entire length and is so selected with respect to its wall thickness that displacing the sleeve along clamping closure 21 results in stronger or weaker closure of tube segment 2 and channel 13. To shield against radioactive media, clamping closure 21 can, in an embodiment of the kind shown in FIG. 6, be made of film-like, radiation-shielding material, for example of a polymer material with a metal vapor-deposited on one or both sides, or entirely of metal.

The novel tube segment can be used in a versatile manner, as the examples show. It also permits improved access for visual probes, manometers and the like into the interiors of cavities. The tube segment even makes it possible to remove fluid or solid fractions from the cavity without the use of special instruments, by causing the interiorly disposed bulge in tube segment 2 to form a sort of lip-like closure merely by pulling on inner wall 4 while simultaneously bracing outer wall 6.

The invention claimed is:

1. A device for tamponade of body cavities and for mechanical anchoring of a catheter having a shaft with an end, the device comprising:
   a flexible tube segment having an inner wall and an outer wall that surround an interior space wherein said tube segment is inflatable to assume a torus geometry with said inner wall defining an internal area, and the internal area is configured without through-passing support bodies so that a displacement of tube wall material between said inner wall and said outer wall of said tube segment is possible as inflation proceeds, wherein said tube segment is preformed in such a way that a tube portion that forms the inner wall of said tube segment after invagination is smaller in cross section and has a greater wall thickness than a tube portion forming the outer wall, and wherein said tube segment further comprises:
   a. two ends, which are fastened to a same closing element, configured so that a torus geometry is striven for as said inflatable tube segment is inflated and
   b. said closing element is a pipe nipple and said two ends of said tube segment are joined together fluid-tightly.

2. The device according to claim 1, wherein at least said outer wall is thin-walled and elastically expandable.

3. The device according to claim 1, wherein at least said outer wall of the tube segment has a wall thickness of a few microns.

4. The device according to claim 1, wherein said tube segment consists of a polyurethane, a polyurethane/polyvinyl chloride mixture, or a comparable polyurethane-based material or a polymer having comparable expansion and processing characteristics.

5. The device according to claim 1, wherein said tube segment is configured for the reversible, sealing securement of the catheter at the end of the catheter shaft.

6. The device according to claim 1, wherein said tube segment is formed by invaginating a single-walled tube section.

7. The device according to claim 6, wherein at least one end of said tube section is attached to the catheter shaft.

8. The device according to claim 1, wherein a channel for the delivery and/or discharge of a fluid opens into the interior space formed by said walls of said tube segment.

9. The device according to claim 6, wherein said tube section or a portion thereof is preformed as a single-walled tube in the shape of a roll before being fashioned into a tube segment by invagination.

10. The device according to claim 9, wherein a bulge produced vertically to the plane of rotation of said tube segment by the invagination is thickened by said preforming.

11. The device according to claim 1, wherein said tube portion is provided with a uniform wall thickness and a uniform inner diameter.

12. The device according to claim 1, wherein said tube segment is implemented with a residual volume.

13. The device according to claim 1, wherein a channel is connected via a flexible connecting tube to a valve disposed outside said tube segment.

14. The device according to claim 13, wherein said valve includes a lip valve.

15. The device according to claim 13, wherein said valve is a circular sleeve consisting of flexible material and disposed between said tube ends.

16. The device according to claim 1, wherein a collar-shaped abutment is disposed on a selected one of said pipe nipple and said catheter shaft.

17. The device according to claim 1, wherein a pressure sensor is contained in the interior space.

18. The device according to claim 1, wherein a medically active substance can be introduced into the interior space enclosed by said tube segment.

19. The device according to claim 18, wherein said medically active substance has at least one of radioactive and chemotherapeutic properties.

20. The device according to claim 18, wherein said tube segment is covered in at least one subregion by a shield and said shield suppresses or decreases the medicinal activity of the substance in the shielded subregion.

21. The device according to claim 1, wherein a radiographic contrast medium can be introduced into the interior space enclosed by said tube segment.

22. The device according to claim 1, wherein affixed to a surface of said tube segment is a pair of electrodes.

23. The device according to claim 1, wherein a receptacle is affixed to the surface of said tube segment.

24. The device according to claim 1, wherein a carrier containing a chemotherapeutic substance is affixed to a surface of said tube segment.

25. The device according to claim 1, wherein a carrier is affixed to a surface of said tube segment.

26. The device according to claim 25, wherein the carrier contains a radioactive substance.

27. A device for tamponade of body cavities and for mechanical anchoring of a catheter, the device comprising:

a flexible tube segment having an inner wall and an outer wall that surround an interior space wherein said tube segment is inflatable to assume a torus geometry with said inner wall defining an internal area, and the internal area is configured without through-passing support bodies so that a displacement of tube wall material between said inner wall and said outer wall of said tube segment is possible as inflation proceeds, wherein said tube segment further comprises:

a. two ends, which are fastened to a same closing element, configured so that a torus geometry is striven for as said inflatable tube segment is inflated and b. said closing element is a pipe nipple and said two ends of said tube segment are joined together fluid-tightly, wherein a clamping closure having a longitudinally displaceable sleeve is slidably attached to said tube segment.

* * * * *